United States Patent [19]
Meier

[11] Patent Number: 5,552,889
[45] Date of Patent: Sep. 3, 1996

[54] METHOD FOR THE POLARIMETRIC EVALUATION OF A POLARIZATION-MODULATED LIGHT SIGNAL

[75] Inventor: Markus Meier, Aarau, Switzerland

[73] Assignee: ABB Research Ltd., Zurich, Switzerland

[21] Appl. No.: 360,036

[22] Filed: Dec. 20, 1994

[30] Foreign Application Priority Data

Dec. 29, 1993 [DE] Germany ............... 43 44 855.0

[51] Int. Cl.[6] ............................................. G01J 4/00
[52] U.S. Cl. ............................... 356/364; 356/367
[58] Field of Search ................................. 356/364–368

[56] References Cited

U.S. PATENT DOCUMENTS 3,700,334  10/1972  Low et al. .
4,589,776   5/1996  Carver et al. ................... 356/367
4,629,323  12/1986  Matsumoto ....................... 356/368
5,311,285   5/1994  Oshige et al. ................... 356/367
5,335,066   8/1994  Yamada et al. .................. 356/367

FOREIGN PATENT DOCUMENTS 2690529  10/1993  France .

OTHER PUBLICATIONS

Stierlin, Roland, "Faseroptische Sensoreu", Optoelektronic, Bulletin SEV/VSE 82, Jan. 1991, pp. 21–29.

Primary Examiner—Frank Gonzalez
Assistant Examiner—Jason D. Eisenberg
Attorney, Agent, or Firm—Burns, Doane, Swecker & Mathis

[57] ABSTRACT

In order to be independent of temperature when evaluating polarization-modulated light signals, DC and AC components from light power signals ($S_1$, $S_2$) are evaluated separately. The algorithm necessary for this purpose is specified.

3 Claims, 1 Drawing Sheet

METHOD FOR THE POLARIMETRIC EVALUATION OF A POLARIZATION-MODULATED LIGHT SIGNAL

BACKGROUND OF THE INVENTION

1. Field of the Invention

The starting point of the invention is a method for the polarimetric evaluation of a polarization-modulated light signal according to the precharacterizing clause of patent claim 1.

2. Discussion of Background

With the precharacterizing clause of patent claim 1, the invention refers to a prior art as is disclosed by Roland Stierlin, Faseroptische Sensoren [Fiber-optic Sensors], Bulletin SEV/VSE 82 (1991), pp. 21–29. In the fiber-optic current sensor described there in conjunction with FIG. 6, the light beam is split into 2 equal parts after passage through a twisted low-birefringent sensor optical fiber. The partial beams each pass through a polarizer onto one photodiode each. The two polarizers are oriented orthogonally to each other, so that without current an equal amount of light goes through both polarizers. If a current flows, the light intensity in the two partial beams changes. A normalized modulation signal is calculated from the ratio of difference and sum of the two photodiode signals.

The twisting of the sensor coil leads to the suppression of the bending-induced linear birefringence. This leads to a temperature-dependent circular birefringence and thus to a temperature-dependent position of the plane of polarization. However, for normal polarimetric detection, the average plane of polarization should be at less than 45° to the two orthogonal polarization filters and detectors. This can be carried out by means of a mechanical adjustment of the polarization unit. In a high-voltage environment, this solution is hardly realizable, because of insulation problems.

U.S. Pat. No. 3,700,334 discloses a 2-beam interferometer polarimeter for measuring the intensity and polarization condition of a light signal. There, the light is subdivided by means of a beam-splitter into 2 partial beams, each of which passes through a polarization filter. The light beams emerging from the polarization filters are sent through a variable delay element, a mixing element and an analyzer, before they are recorded in a sensor unit and evaluated.

SUMMARY OF THE INVENTION

Accordingly, one object of the invention, as it is defined in patent claim 1, is to provide a novel method for the polarimetric evaluation of a polarization-modulated light signal of the type cited at the beginning in such a way that a measurement of a physical or chemical variable, which measurement is independent of temperature influences, is possible at low cost.

One advantage of the invention resides in the fact that no temperature compensation device is necessary.

By means of the arrangement of 2 or more polarization filters, which are not orthogonal, or not only orthogonal, to each other, it can be achieved that a polarimetric modulation signal is always obtained from one or from a plurality of photodetectors. The intensity of this modulation signal, in the case of a constant measuring signal, is a function of the position of the average plane of polarization. By evaluating the alternating component of the light power signals of all photodetectors which is normalized to the respective constant component, according to amount and phase, the position of the direction of polarization can be determined. From this knowledge, the respective light power signal most favorable for the evaluation can then be read out and corrected according to amount and phase.

According to an advantageous refinement of the invention, a combination of a plurality of light power signals can be evaluated. With knowledge of the position of the direction of polarization, the polarimeter signal can be exactly linearized. In this way, distortions of the measuring signal are avoided, and intermodulations of the harmonics of the mains frequency in the case of measurements on a power supply system.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
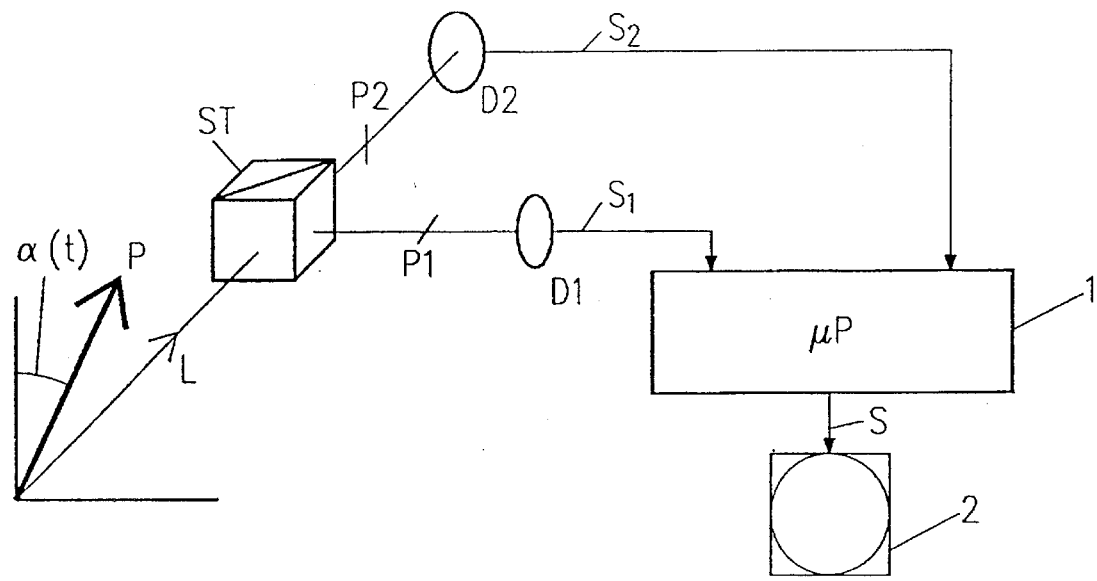
FIG. 1 shows a representation of the principle of an evaluation device of a polarization-modulated light signal and FIGS. 2 and 3 show alternative directions of polarization for evaluating in a manner analogous to FIG. 1.

Referring now to the drawings, wherein like reference numerals designate identical or corresponding parts throughout the several views, FIG. 1 shows a polarization-modulated light beam (L), which, for example, comes from a magneto-optical Faraday rotator or from a fiber-optic current sensor (not shown) with a direction of polarization (P) at an angle of polarization ($\alpha(t)$) with respect to an average position of the plane of polarization $\alpha_0$ and falls onto a beam-splitter (ST) and is there separated into 2 partial beams. The two partial beams pass through 1st and 2nd polarization filters (P1, P2) aligned orthogonally to each other to 1st and 2nd photodetectors or photodiodes (D1, D2), respectively, which on the output side supply 1st and 2nd light power signals ($S_1$, $S_2$), respectively, after conversion into voltage signals and digital signals (not shown) proportional thereto, to a microprocessor or computer (1) for evaluation. On the output side, the latter supplies a modulation signal (S) independent of the position of the plane of polarization $\alpha_0$ to an output or display device (2). The two 1st polarization filters (P1, P2) act as analyzers.

Hereinafter, the evaluation of the light power signals ($S_1$, $S_2$) carried out in the computer (1) is described.

At a general position of the plane of polarization at the angle of polarization ($\alpha(t)$), the light power signals ($S_1$, $S_2$) are given by the following expressions:

$$S_1 = a_1 \cdot 0.5 \cdot (1 + \cos(2 \cdot \alpha(t))) \tag{1}$$

$$S_2 = a_2 \cdot 0.5 \cdot (1 + \cos(2 \cdot \alpha(t))) \tag{2}$$

where $$\alpha(t) = \alpha_0 + \alpha_F \cdot \cos(\omega \cdot t) \tag{3}$$

$$\alpha_F = V \cdot I_0 \tag{4}$$

=Faraday angle, caused by the measuring signal, for example by a current I, $I_0$=maximum value of I, V=Verdet constant, $\omega$=angular velocity of the mains frequency or of the alternating components of $S_1$ and $S_2$, $$I(t)=I_0 \cdot \cos(\omega \cdot t), \quad (5)$$

$a_1, a_2$=gain factors of transmission channels in the beam path of the 1st and 2nd partial beam, respectively.

From these, the following constant components, designated by DC, and alternating components, designated by AC, can be obtained from the light power signals ($S_1$, $S_2$):

$$S_{1,DC}=a_1 \cdot 0.5 \cdot (1+\cos(2 \cdot \alpha_0)), \quad (6)$$

$$S_{2,DC}=a_2 \cdot 0.5 \cdot (1-\cos(2 \cdot \alpha_0)), \quad (7)$$

$$S_{1,AC}=-a_1 \cdot \alpha_F \cdot \sin(2 \cdot \alpha_0) \cdot \cos(\omega \cdot t), \quad (8)$$

$$S_{2,AC}=a_2 \cdot \alpha_F \cdot \sin(2 \cdot \alpha_0) \cdot \cos(\omega \cdot t). \quad (9)$$

Using the abbreviations:

$$A_{1,AC}=a_1 \cdot \alpha_F \cdot \sin(2 \cdot \alpha_0)$$

and $$A_{2,AC}=a_2 \cdot \alpha_F \cdot \sin(2 \cdot \alpha_0)$$

the quotients Q1, Q2 and Q can be formed in accordance with:

$$\begin{aligned}
Q1 &= A_{1,AC}/S_{1,DC} & (10) \\
&= \alpha_F \cdot \sin(2 \cdot \alpha_0)/[1+\cos(2 \cdot \alpha_0)], \\
Q2 &= A_{2,AC}/S_{2,DC} & (11) \\
&= \alpha_F \cdot \sin(2 \cdot \alpha_0)/[1-\cos(2 \cdot \alpha_0)], \\
Q &= Q1/Q2 = 1-\cos(2 \cdot \alpha_0)/[1+\cos(2 \cdot \alpha_0)]. & (12)
\end{aligned}$$

From these, the average position of the plane of polarization $\alpha_0$ is obtained in accordance with:

$$\begin{aligned}
\alpha_0 &= 0.5 \cdot \arccos(1-Q)/(1+Q) & (13) \\
&= \arccos(Q2-Q1)/(Q2+Q1).
\end{aligned}$$

Hence, the modulation signal (S) independent of this position and of the gain factors $a_1$ and $a_2$ can be determined in accordance with:

$$\begin{aligned}
S &= ((S_{2,AC}-S_{1,AC})/\sin(2 \cdot \alpha_0))/(S_{1,DC}+S_{2,DC}) & (14) \\
&= \alpha_F \cdot \cos(\omega \cdot t).
\end{aligned}$$

Because of the factor $1/\sin(2 \cdot \alpha_0)$, $\alpha_0$ must not approach too closely to the values $0°$ and $90°$.

If, as the result of a switch-on process, the Faraday angle $\alpha_F$ begins suddenly to change from a quiescent angle or from the average position of the plane of polarization $\alpha_0$, then the evaluation using the method of the AC/DC quotients can no longer be carried out. In the place of the AC values, the instantaneous 1st derivatives of the light power signals ($S_1$, $S_2$) then occur. Hence, the same expressions as in the Taylor expansion of equations (8) and (9) occur once more. The angle $\alpha(t)$ can once more be obtained from a quotient and arccos operation. The modulation signal (S) is then formed as the difference from the 1st $\alpha$-value occurring.

If the angle $\alpha_0$ deviates from $45°$, then the Taylor expansions of equations (8) and (9) around the point $\alpha_0$ still contain elements also having even powers (2nd, 4th, ... ) of the modulation signal (S). These even powers, however, lead, owing to their "rectifier effect", to contributions to the DC component which do not directly come from the terms:

$$S_{1,DC}=a_1 \cdot 0.5 \cdot (1+\cos(2 \cdot \alpha_0))$$

and $$S_{2,DC}=a_2 \cdot 0.5 \cdot (1-\cos(2 \cdot \alpha_0)).$$

As a consequence, the calculation of the angle $\alpha_0$ is falsified, if it is carried out according to equation (13).

Figure 2:
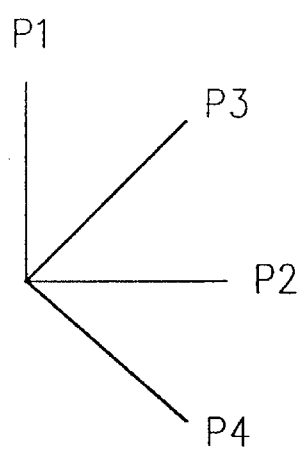

An extension of the angular range of $\alpha_0$ can be achieved by the addition of further polarization channels. To the directions of polarization (P1, P2) according to FIG. 1, the orthogonal, but rotated by $45°$, pair (P3, P4) can be added, cf. FIG. 2. For this purpose, the two partial beams are led from the output of the beam-splitter (ST) via in each case one further beam-splitter, not shown. In this way it is achieved that the direction of polarization (P) always lies within $\pm 22.5°$ with respect to the angular bisector of a polarization system. By means of an evaluation of the light power signals of both detector pairs, the most favorable signal pair in each case can be evaluated by means of a logic circuit, that is to say that signal pair for which the above-specified condition ($\pm 22.5°$) is fulfilled.

Figure 3:
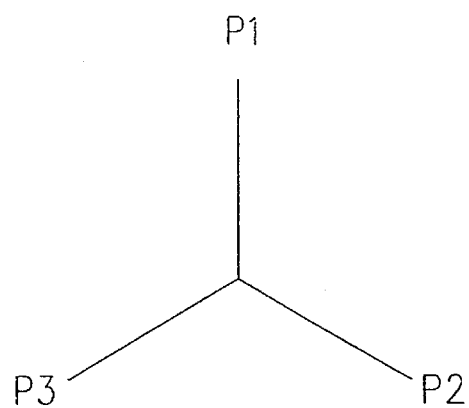

A further possibility is the arrangement of the polarization filters (P1, P2, P3) at a mutual angle of $120°$, cf. FIG. 3. For this purpose, one of the two partial beams is led from the output of the beam-splitter (ST) via a further beam-splitter, not shown. Here, the respectively most favorable signal pair (P1, P2; P2, P3; P3, P4) must be determined and used for the evaluation, that is to say that signal pair for which the direction of polarization (P) lies within $\pm 30°$ of the angular bisector of the polarization pair.

Obviously, numerous modifications and variations of the present invention are possible in light of the above teachings. It is therefore to be understood that within the scope of the appended claims, the invention may be practiced otherwise than as specifically described herein.

What is claimed is:

1. A method for polarimetric evaluation of a polarization-modulated light signal, comprising steps of:

a) splitting light with a direction of polarization with respect to a plane of polarization $\alpha 0$ in a beam-splitter into two partial beams, b) subsequently deflecting the partial beams via polarization filters onto photo-detectors, c) which photodetectors supply, on an output side, light power signals ($S_1$, $S_2$) proportional to received light power, d) a DC component $S_{1,DC}$, $S_{2,DC}$ and an AC component $S_{1,AC}$, $S_{2,AC}$ being derived from each of these light power signals ($S_1$, $S_2$), and e) the DC components $S_{1,DC}$, $S_{2,DC}$ and the AC components $S_{1,AC}$, $S_{2,AC}$ being ratioed to each other, wherein f) a modulation signal S is formed and output in accordance with:

$$S=((S_{2,AC}-S_{1,AC})/\sin(2 \cdot \alpha_0))/(S_{1,DC}+S_{2,DC})$$

where $$S_{1,AC}=-a_1 \cdot \alpha_F \cdot \sin(2 \cdot \alpha_0) \cdot \cos(\omega \cdot t),$$

$$S_{2,AC}=a_2 \cdot \alpha_F \cdot \sin(2 \cdot \alpha_0) \cdot \cos(\omega \cdot t),$$

$$S_{1,DC}=a_1 \cdot 0.5 \cdot (1+\cos(2 \cdot \alpha_0)),$$

$$S_{2,DC}=a_2 \cdot 0.5 \cdot (1-\cos(2 \cdot \alpha_0)),$$

and wherein $\alpha_F$=angle of rotation produced by a physical or chemical variable, $\alpha_0$=angle which defines a plane of polarization, $\omega$=angular velocity of $S_{1,AC}$ and $S_{2,AC}$, and $a_1$, $a_2$=gain factors of light transmission channels.

2. The method as claimed in claim 1, further comprising steps of:
 a) subdividing the polarization-modulated light signal to be evaluated into four partial beams,
 b) each pair of two of the four partial beams being polarized orthogonally to each other such that two orthogonal pairs of partial beams are produced,
 c) rotating directions of polarization (P1, P2; P3, P4) of the two orthogonal pairs of partial beams by 45° relative to each other,
 d) separately evaluating the light power signals ($S_1$, $S_2$) derived from the partial beams per signal pair, and
 e) selecting a signal pair from among said two orthogonal pairs for which the direction of polarization of the polarization-modulated light signal lies within ±22.5° with respect to an angular bisector of the signal pair for forming the modulation signal (S).

3. The method as claimed in claim 1, further comprising steps of:
 a) separately evaluating light power signals from three directions of polarization (P1–P3), which are rotated by 120° each relative to each other, and
 b) selecting a signal pair (P1, P2; P2, P3; P3, P4) from among orthogonal pairs of partial beams obtained from said polarization-modulated light signal for which a direction of polarization (P) of the light lies within ±30° of an angular bisector of the signal pair for forming the modulation signal (S).

* * * * *